(12) United States Patent
Ehmig et al.

(10) Patent No.: US 9,770,397 B2
(45) Date of Patent: Sep. 26, 2017

(54) OXIDATIVE DYEING COMPOSITION

(71) Applicant: KAO GERMANY GMBH, Darmstadt (DE)

(72) Inventors: Jürgen Ehmig, Darmstadt (DE); Manuella Jourdan, Darmstadt (DE); Sandra Schmelz, Darmstadt (DE); Martin Uellner, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 64 days.

(21) Appl. No.: 14/898,619

(22) PCT Filed: Dec. 13, 2013

(86) PCT No.: PCT/EP2013/076479
§ 371 (c)(1),
(2) Date: Dec. 15, 2015

(87) PCT Pub. No.: WO2015/180740
PCT Pub. Date: Dec. 3, 2015

(65) Prior Publication Data
US 2016/0184205 A1    Jun. 30, 2016

(30) Foreign Application Priority Data
Dec. 20, 2012  (EP) .................... 12198697

(51) Int. Cl.
| *A61Q 5/10* | (2006.01) |
| *A61K 8/44* | (2006.01) |
| *A61K 8/34* | (2006.01) |
| *A61K 8/41* | (2006.01) |

(52) U.S. Cl.
CPC .............. *A61K 8/445* (2013.01); *A61K 8/342* (2013.01); *A61K 8/41* (2013.01); *A61Q 5/10* (2013.01); *A61K 2800/882* (2013.01)

(58) Field of Classification Search
CPC . A61Q 5/10; A61K 8/41; A61K 8/342; A61K 2800/882
See application file for complete search history.

(56) References Cited

U.S. PATENT DOCUMENTS

| 8,409,552 B2 | 4/2013 | Schumas et al. |
| 2007/0224154 A1 | 9/2007 | Brumbaugh |
| 2009/0297468 A1* | 12/2009 | Vielhaber .............. A61K 8/445 424/73 |
| 2010/0286102 A1* | 11/2010 | Vielhaber ................ A61K 8/34 514/171 |

FOREIGN PATENT DOCUMENTS

| DE | 102 54 872 A1 | 6/2004 | |
| WO | 2006/134120 A1 | 12/2006 | |
| WO | WO 2012/089648 A1 * | 7/2007 | .............. A61Q 5/10 |
| WO | 2012/089648 A1 | 7/2012 | |

OTHER PUBLICATIONS

International Search Report and Written Opinion of the ISA dated Sep. 25, 2015, mailed Oct. 9, 2015.

* cited by examiner

*Primary Examiner* — Eisa Elhilo
(74) *Attorney, Agent, or Firm* — Norris McLaughlin & Marcus PA

(57) ABSTRACT

Present invention relates to an oxidative dyeing composition having especially mild properties to the scalp. The object of the present invention is an oxidative dyeing composition for hair comprising at least one dyestuff and avenathramide and/or its derivative.

21 Claims, No Drawings

OXIDATIVE DYEING COMPOSITION

This application is a §371 U.S. National stage of PCT International Patent Application No. PCT/EP2013/076479, filed Dec. 13, 2013, which claims foreign priority benefit of European Patent Application No. EP 12198697.0, filed Dec. 20, 2012, the disclosures of each of which patent applications are incorporated herein by reference.

Present invention relates to an oxidative dyeing composition having especially mild properties to the scalp.

Oxidative hair dyeing is carried out using oxidative dyes in the presence of oxidizing agent under weak to strong alkaline conditions. It is common to use ammonium hydroxide in such compositions. However, it has a strong disturbing smell and there has always been a desire to use alkalizing agents which does not have such disturbing smell.

Alkyl or alkanol amine type of alkalizing agents has also been used instead of ammonium hydroxide as an alkalizing agent despite some drawbacks in dyeing effect. Additionally it has been observed that the use of alkyl or alkanolamine type of alkalizing agent has brought further drawbacks on mildness of the compositions.

Present invention aims at providing an oxidative dyeing composition with acceptable mildness on scalp.

The inventors of the present invention have surprisingly found out that an oxidative hair dyeing composition comprising avenanthram ides is especially mild to scalp.

Avenanthramides have been proposed and used in scalp care and conditioning compositions. It has never been suggested that it may improve mildness of an oxidative dyeing composition which has slight to strong alkaline pH.

The first object of the present invention is an oxidative dyeing composition for hair comprising at least one dyestuff and avenanthramide and/or its derivative.

The second object of the present invention is the use of the composition for colouring hair.

The third object of the present invention is the method of colouring hair wherein a composition according to present invention is mixed with another composition comprising at least one oxidizing agent and applied onto hair and after processing 1 to 45 min rinsed off from hair.

Since the compositions of the present invention are in general mild to strong alkaline, it may be that avenanthramide and/or its derivatives do not have the optimum long term stability under such conditions so that in order to secure the optimum benefits of the presence of avenanthramide and/or its derivative it may become necessary that avenanthramide and/or its derivative is added prior to use to a composition comprising at least one oxidative dyestuff and oxidizing agent. Therefore, the fourth object of the present invention is that a method for colouring hair wherein avenanthramide and/or it derivatives is added to a composition obtained by mixing a composition comprising at least one dyestuff and a composition comprising at least one oxidizing agent and the resulting composition is applied onto hair and after processing of 1 to 45 min rinsed off from hair.

Another object of the present invention is that a kit for colouring hair comprising two or more compositions wherein one of the compositions comprises at least one oxidative dyestuff and avenanthramide and/or its derivative and another composition comprising at least one oxidizing agent. As stated in the above paragraph the kit can comprise a third composition which comprises avenanthramide and/or its derivative.

Compositions of the present invention preferably an aqueous composition and comprises at least 45%, preferably in the range of 50 to 90% and more preferably in the range of 55 and 85% and most preferably in the range of 60 to 80% by weight water calculated to the total composition.

Compositions of the present invention comprise at least one dyestuff selected from oxidative dyestuffs precursors and direct dyes. Suitable oxidative dyestuffs precursors are tetraaminopyrimidines, in particular 2,4,5,6-tetraaminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof, aminophenol derivatives such as 4-aminophenol, 4-amino-3-methylphenol, 2-chloro-4-aminophenol, 2,6-dichloro-4-aminophenol, 2,4-diaminophenol, 2,6-dibromo-4-aminophenol and/or 2-aminophenol and water-soluble salts thereof, furthermore, phenylenedimanine derivatives such as 2,5-diamino-toluene, 2-n-propyl or 2-ethyl-p-phenylene-diamine, 2,6-dimethyl-p-phenylene-diamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene or the water-soluble salts thereof, pyrazole derivatives such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 1-methyl-4,5-diaminopyrazole, 1-methylethyl-4,5-diaminopyrazole, 1-phenylmethyl-4,5-diaminopyrazole, 1-methyl-4,5-diaminopyrazole, 1-(4-methylphenyl)methyl-4,5-diaminopyrazole, 1-methyl-3-phenyl-4,5-diaminopyrazole and the water-soluble salts. The use of the above mentioned oxidative dye precursors as mixture is also customary in hair coloring area.

The composition according to the invention optionally but preferably comprises at least one coupling substance, which can be selected from resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxypyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1.2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances. In the preferred embodiment of the present invention composition comprise additionally at least one coupling agent.

The weight proportion of the developing substances to the coupling substances ranges between about 1:8 to 8:1, preferably about 1:5 to 5:1, in particular 1:2 to 2:1.

The composition of the present invention comprises direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57, Basic yellow 87 and Basic orange 31. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Additional suitable direct dyes are of the following chemical structures.

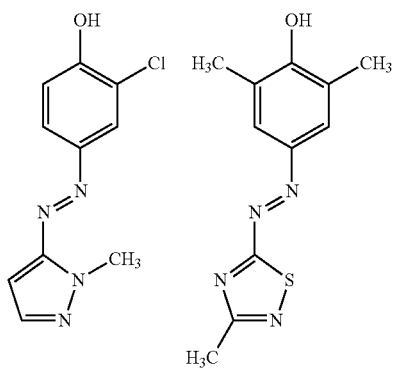

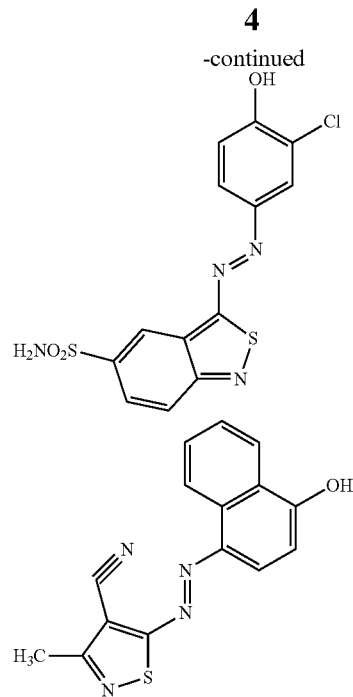

Some examples to those suitable neutral dyes (HC dyes), so called nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

According to the invention, the coloring composition comprises hair dyes at a total concentration of 0.001 to 15%, preferably 0.01 to 12.5%, more preferably 0.05 to 10%, most preferably 0.1 to 7.5% by weight calculated to total composition.

Compositions of the present invention comprise avenanthramide and/or its derivative. Suitable and preferred are avenanthramide A, avenanthramide B, avenanthramide, dihydroavenanthramide A, dihydroavenanthramide B, dihydroavenanthramide C, and hydroxyphenly propamidobenzoic acid. Particularly preferred is hydroxyphenly propamidobenzoic acid Compositions comprise avenanthramide and/or its derivative at a total concentration of 0.0001 to 5%, preferably 0.001 to 4%, more preferably 0.005 to 3% and most preferably 0.01 to 2.5% and in particular 0.1 to 1.5% by weight calculated to the total composition.

The compositions of the present invention are preferably emulsions and preferably comprise one or more fatty alcohol, preferably of the general formula $$R_4\text{—OH}$$

wherein $R_4$ is a linear or branched, saturated or unsaturated alkyl chain with 12 to 22 C atoms and at least one emulsifier preferably selected from anionic, non-ionic, cationic and amphoteric surfactants.

Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 2.5 to 20%, more preferably 5 to 15% and most preferably 5 to 10% by weight calculated to total composition.

The composition of the present invention comprises at least one surfactant, preferably selected from anionic, non-ionic, cationic and amphoteric surfactants. Preferred surfactants are anionic, non-ionic and cationic ones and especially preferred are anionic and/or non-ionic surfactants. Preferred mixing ratio for the anionic—non-ionic emulsifying surfactant mixture is in the range of 5:1 to 1:5, more preferably 3:1 to 1:3 and especially 1:1, by weight.

In principal any anionic surfactant is suitable within the meaning of the present invention. Nonlimiting examples are anionic surfactants of the sulfate, sulfonate, carboxylate and alkyl phosphate type, especially, of course, those customarily used as emulsifiers, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolam ides, and the alkali salts thereof, as well as the salts of long-chain mono- and dialkyl phosphates and their salts.

Further suitable surfactants of the carboxylate type are alkyl polyether carboxylic acids and the salts thereof of the formula $$R_5\text{—}(C_2H_4O)_n\text{—O—}CH_2COOX,$$

wherein $R_5$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula $$R_5\text{—}\underset{\underset{O}{\|}}{C}\text{—}\underset{\underset{H}{|}}{N}\text{—}CH_2\text{—}CH_2\text{—}(C_2H_4O)_n\text{—}CH_2COOX$$

wherein $R_5$ and X have the above meanings, and n is in particular a number from 1 to 10, preferably 2.5 to 5.

Among the anionic surfactants most preferred are alkyl sulfates and/or alkyl ether sulfates and among them sodium lauryl or laureth sulfates and their mixtures are most preferred.

Suitable non-ionic surfactants are alkyl polyglucosides of the general formula $$R_6\text{—O—}(R_7O)_n\text{O—}Z_x$$

wherein $R_6$ is an alkyl group with 8 to 18 carbon atoms, $R_7$ is an ethylene or propylene group, Z is a saccharide group with 5 to 6 carbon atoms, n is a number from 0 to 10 and x is a number between 1 and 5. Examples are decyl polyglucoside and cocoyl polyglucoside, both being commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

Among the non-ionic surfactants mentioned above fatty alcohol ethoxylates and fatty acid alkanolam ides and their mixtures at any weight ratio are the most preferred ones.

As a rule any mono alkyl quaternary ammonium surfactants is suitable for the compositions of the present invention as cationic emulsifying surfactant. With the term mono alkyl it is meant that quaternary ammonium surfactant includes only 1 alkyl chain which has more than 8 C atoms. The term does not exclude that the quaternary ammonium surfactant includes further short alkyl chains, $C_1$ to $C_4$, present in the molecule.

Preferably at least one mono alkyl quaternary ammonium surfactant is selected from the compounds with the general formula $$R_{10}\text{—}\underset{\underset{R_{11}}{|}}{\overset{\overset{R_8}{|}}{N^+}}\text{—}R_9 \quad X^-$$

where $R_8$ is saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has typical value of 0-4 or $$R_{12}COO(CH_2)_n$$

where $R_{12}$ is saturated or unsaturated, branched or non-branched alkyl chain with 7-21 C atoms and n has typical value of 0-4, and $R_9$, $R_{10}$ and $R_{11}$ are independent from each other lower alkyl chain with 1 to 4 carbon atoms, hydroxyl alky chain with 1 to 4 C atoms, or ethoxy or propoxy group with number of ethoxy or propoxy groups varying in the range of 1 to 4, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, stear trimonium chloride, stearamidopropyltrimethylammonium chloride, stearamidopropyl trimonium chloride.

Surfactants are included into the compositions of the present at a total concentration of 0.5 to 20%, preferably 1 to 15% and more preferably 1.5-12.5%, and most preferably 2 to 10% by weight, calculated to the total composition.

Compositions of the present invention have a pH in the range of 6 to 12 and preferably 6.5 to 11, more preferably 6.8 to 11 and most preferably 8 to 10.5 and in particular 9 to 10.

Compositions are therefore comprised at least one alkalizing agent especially when the pH is in the neutral to alkaline range. Suitable alkalizing agents are sodium hydroxide, ammonia or ammonium hydroxide and a compound according to the general formula $$R_1R_2R_3N$$

wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is a mono or polyhydroxyalkyl. Preferably $R_1$, $R_2$ and $R_3$ are same or different H, C1-C4 alkyl, C1-C4 monohydroxyalkyl or C2-C4 polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine. Ammonia and sodium hydroxide are also preferred as an alkalizing agent.

Within the meaning of the present invention it should also be understood that oxidative dyeing compositions and/or ready to use oxidative dyeing compositions can comprise more than one alkanolamine such as a mixture of two or three alkanolamines.

The concentration of at least one alkalizing agent varies between 0.25 and 35%, preferably 1 and 30, more preferably 2.5 and 25 and most preferably 2.5 to 20% by weight calculated to the total composition.

Composition of the present invention comprises at least one oxidizing agent. The oxidizing agents suitable are hydrogen peroxide, urea peroxide, melamin peroxide or perborate salts. The preferred oxidizing agent is hydrogen peroxide, at a concentration in a range of 2 to 12% by weight calculated to the total composition.

At the same time, the kit of above preferably comprises an additional composition comprising at least one oxidizing agent, preferably hydrogen peroxide.

The pH of the composition comprising at least one oxidizing agent is in the range of 1.5 to 5, preferably 2.5 to 4 and more preferably 3 to 4.

The hair dyeing compositions can comprise an organopolysiloxane wherein at least one silicon atom is linked to an alkylene group having a hetero-atom, in particular a nitrogen atom, with a poly-(N-acyl alkyleneimine) units of the formula

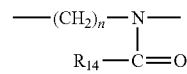

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

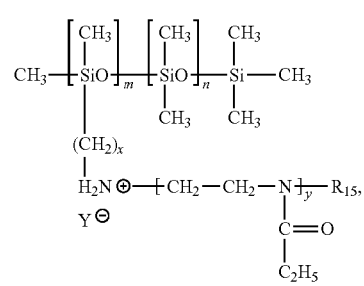

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Another compound that may be comprised in the colouring composition is a ceramide type of compounds according to the general formula

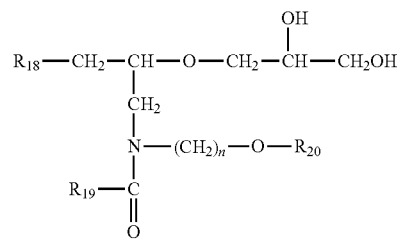

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6, preferably 2 or 3. The concentration of the ceramide type of compound in colouring compositions of the present invention can be in the range of 0.01 to 2 and especially 0.01 to 1% by weight calculated to the total composition.

The compositions according to the present invention can further comprise one or more ubiquinone of the formula.

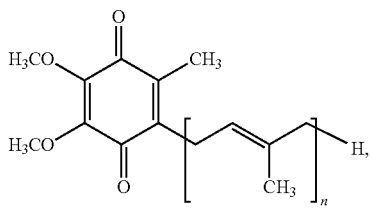

wherein n is a number from 1 to 10. The concentration of ubichinones in the compositions of the present invention can vary between 0.001% and 10% by weight, calculated to the total composition excluding the oxidizing agent.

The coloring composition of the present invention can certainly comprise compounds for accelerating (catalysts) the oxidative dyeing keratin fibres such as iodine salts i.e. potassium or sodium iodide and/or dihydroxy acetone.

Further compositions can comprise yogurt powder at a concentration of 0.01 to 5% by weight calculated to total composition prior to mixing with oxidizing agent, which is a raw material prepared by spray drying of natural yoghurt after completion of fermentation. Yogurt powder comprises the following major components:

approximately 53.5% lactose,
approximately 25% proteins,
approximately 7.5% lactic acid,
approximately 5% minerals and trace elements,
approximately 1% vitamines, and
approximately 2% lipids.

Compositions of the present invention can comprise additionally hair conditioning compounds such as additional oils, cationic polymers, non-ionic substances. Oils as conditioners according to the present invention are selected from silicone oils either volatile or non-volatile, natural and synthetic oils. Among silicone oils those can be added to the compositions include either volatile or non-volatile dimethicone, dimethiconol, polydimethylsiloxane, any arylated silicones such as phenyl trimethicone, DC fluid ranges from Dow Corning, cyclosiloxanes such as DC 245. Synthetic oils include mineral oil such as paraffin oil and petrolatum.

Natural oils suitable are such as argan oil, marula oil, olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are also suitable for the composition of the present invention. Examples are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

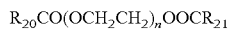

where $R_{20}$ and $R_{21}$ are independent from each other saturated, unsaturated or branched or non-branched alkyl chain with 7 to 21 C atoms and n is typically 2-100.

Composition of the present invention can comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

Concentration range for any of the additional conditioners mentioned above is in the range of 0.01 to 10% by weight, preferably 0.05-7.5% by weight, more preferably 0.1-5% by weight calculated to the total composition.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol®". Extracts and the preparation thereof are also described in "Hagers Handbuch der pharmazeutischen Praxis", $4^{th}$ Ed.

Compositions of the present invention may further comprise particulate matter such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

The hair dyeing compositions according to the invention can comprise basic substances and additives customarily found in such compositions, such as conditioning agents, reducing agents and stabilizers for oxidizing agent, foam preventing agents etc., known as state of the art.

The following examples are to illustrate the invention without limiting it.

EXAMPLE 1

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Hydroxyphenyl propamidobenzoic acid | 0.1 |
| 2,5,6-Triamino-4-hydroxypyrimidinsulfat | 0.01 |
| 2,5-Diaminotoluolsulfat | 0.55 |
| 4-Chlorresorcin | 0.17 |
| Resorcin | 0.05 |
| 3-Aminophenol | 0.03 |
| Sodium sulfite | 1.0 |
| Monoethanolamine | 8.0 |
| Fragrance, preservative | q.s. |
| Water | to 100 |

For comparative purposes the same composition but not comprising hydroxyphenyl propamidobenzoic acid was also produced. Hydroxyphenyl propamidobenzoic acid was pre-placed with water.

The above compositions were tested in a monadic use test for scalp compatibility and mildness. Both compositions were used to dye hair of 30 consumers each having shoulder length hair. The composition was mixed with a composition comprising 6% hydrogen peroxide at a weight ratio of 1 to 1 and applied onto hair and processed for 30 min at a temperature of 40° C. and rinsed off. It was observed that both composition colour hair in the same way to the same colour direction. The following observations were made on scalp irritation.

|  | No irritation | Slight irritation | Irritation |
| --- | --- | --- | --- |
| Inventive composition | 24 | 4 | 2 |
| Comparative composition | 2 | 13 | 15 |

From the above results it is clear that hydroxyphenyl propamidobenzoic acid comprising composition does not cause that much irritation compared to comparative composition without hydroxyphenyl propamidobenzoic acid. The clear conclusion from the above results is that incorporation of hydroxyphenyl propamidobenzoic acid improved mildness of hair dyeing composition and improved scalp compatibility.

The invention claimed is:

1. An oxidative dyeing composition comprising:
   at least one dyestuff selected from oxidative dyestuff precursors and direct dyes, and
   one or both of: avenanthramide and a derivative thereof,
   wherein the avenanthramide, its derivative, or a mixture thereof is present at a total concentration of 0.0001 to 5% by weight calculated to the total composition.

2. The composition according to claim 1, wherein the composition is an aqueous composition and comprises at least 45% by weight water calculated to the total composition.

3. The composition according to claim 1, further comprising at least one oxidative dyestuff precursor and at least one coupling agent.

4. The composition according to claim 1, said composition comprising at least one direct dye.

5. The composition according to claim 1, comprising an avenanthramide derivative selected from avenanthramide A, avenanthramide B, avenanthramide, dihydroavenanthramide A, dihydroavenanthramide B, dihydroavenanthramide C, hydroxyphenly propamidobenzoic acid, salts thereof, and mixtures thereof.

6. The composition according to claim 1, which comprises hydroxyphenyl propamidobenzoic acid, salts thereof, or mixtures thereof.

7. The composition according to claim 1, which further comprises one or more fatty alcohol
and at least one emulsifier.

8. The composition according to claim 1, which further comprises one or more fatty alcohol selected from myristyl alcohol, cetyl alcohol, stearyl alcohol behenyl alcohol and a mixture thereof.

9. The composition according to claim 1, which further comprises at least one emulsifier present at a total concentration in the range of 0.5 to 20% by weight, calculated to the total composition.

10. The composition according to claim 1, having a pH in the range of 6 to 12.

11. The composition according to claim 1, which further comprises at least one alkalizing agent selected from ammonia or ammonium hydroxide and a compound according to the general formula $R_1R_2R_3N$ wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is a mono or polyhydroxyalkyl.

12. The composition according to claim 11, wherein the at least one alkalizing agent is ammonia or monoethanolamine.

13. A method of colouring hair comprising:
(a) mixing a composition according to claim 1 with a second composition comprising at least one oxidizing agent,
(b) applying onto hair a mixture obtained from step (a),
(c) processing the mixture obtained from step (a) for 1 to 45 min,
(d) rinsing the mixture obtained from step (a) off from hair.

14. The composition according to claim 2, comprising water in the range of 50 to 90% by weight calculated to the total composition.

15. The composition according to claim 1, wherein the avenanthramide, its derivative, or mixture thereof is present at a total concentration of 0.001 to 4% by weight calculated to the total composition.

16. The composition according to claim 7, wherein the one or more fatty alcohol is of the general formula $$R_4\text{—OH}$$

wherein $R_4$ is a linear or branched, saturated or unsaturated alkyl chain with 12 to 22 C atoms.

17. The composition according to claim 7, wherein the at least one emulsifier is selected from anionic, non-ionic, cationic and amphoteric surfactants.

18. The composition according to claim 8, wherein the one or more fatty alcohol is a mixture of cetyl and stearyl alcohol.

19. The oxidative dyeing composition of claim 1 in the form of an emulsion.

20. The oxidative dyeing composition of claim 1 consisting essentially of:
at least one dyestuff selected from oxidative dyestuff precursors and direct dyes, and
one or both of: avenanthramide and a derivative thereof, and
one or more of optional components (a) through (t):
(a) one or more coupling substances,
(b) one or more fatty alcohols,
(c) one or more emulsifiers and/or surfactants,
(d) one or more alkalizing agents,
(e) one or more oxidizing agents,
(f) one or more organopolysiloxanes, wherein at least one silicon atom is linked to an alkylene group having a hetero-atom,
(g) one or more ceramide compounds according to the general formula

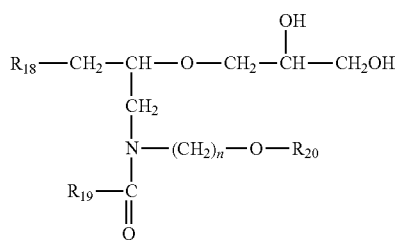

where $R_{18}$ and $R_{19}$ are independent from each other alkyl- or alkenyl group with 10 to 22 carbon atoms, $R_{20}$ is methyl, ethyl, n-propyl or isopropyl group and n is a number between 1 to 6,
(h) one or more ubiquinone of the formula

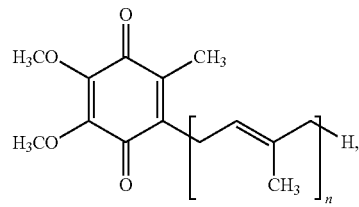

wherein n is a number from 1 to 10,
(i) one or more catalyst for oxidative dyeing of keratin fibers,
(j) one or more yogurt powders,
(k) one or more hair conditioning compounds,
(l) one or more cationic polymer conditioning agents,
(m) one or more protein hydrolysates,
(n) one or more natural plant extracts,
(o) one or more particulate matters,
(p) one or more basic substances,
(q) one or more conditioning agents,
(r) one or more reducing agents,
(s) one or more stabilizers for oxidizing agents, and
(t) one or more foam preventing agents.

21. An oxidative dyeing composition comprising:
(a) at least one dyestuff selected from oxidative dyestuff precursors and direct dyes,
(b) one or both of: avenanthramide and a derivative thereof,
wherein (b) includes hydroxyphenyl propamidobenzoic acid, salts thereof, or mixtures thereof.

* * * * *